United States Patent [19]
Ohara et al.

[11] Patent Number: 5,514,804
[45] Date of Patent: May 7, 1996

[54] DIASTEREOMER SALT OF OPTICALLY ACTIVE QUINOLINEMEVALONIC ACID

[75] Inventors: Yoshio Ohara; Mikio Suzuki; Yoshinobu Yanagawa; Hiroshi Iwasaki; Nobuhide Miyachi, all of Funabashi, Japan

[73] Assignee: Nissan Chemical Industries Ltd., Tokyo, Japan

[21] Appl. No.: 450,383

[22] Filed: May 25, 1995

Related U.S. Application Data

[62] Division of Ser. No. 123,117, Sep. 20, 1993, which is a division of Ser. No. 902,863, Jun. 23, 1992, Pat. No. 5,284,953.

[30] Foreign Application Priority Data

Jun. 24, 1991 [JP] Japan ................................ 3-151810
May 20, 1992 [JP] Japan ................................ 4-127277

[51] Int. Cl.⁶ .................................................. C07D 405/06
[52] U.S. Cl. .................................................. 546/173
[58] Field of Search ................................ 546/173

[56] References Cited

U.S. PATENT DOCUMENTS 3,897,436  7/1975  Goschke ................................ 546/173
4,567,289  1/1986  Willard et al. ......................... 560/59

*Primary Examiner*—Shean C. Wu
*Assistant Examiner*—Catherine Kilby Scalzo
*Attorney, Agent, or Firm*—Oblon, Spivak, McClelland, Maier & Neustadt

[57] ABSTRACT

A diastereomer salt of optically active quinolinemevalonic acid of the formula ((−)I·(+)II):

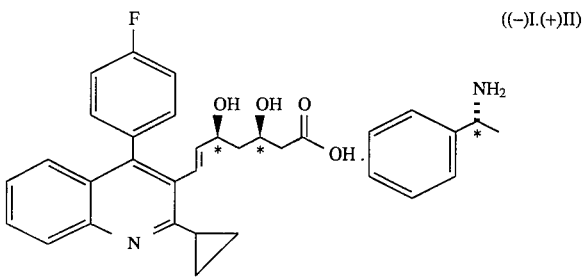

((−)I·(+)II)

8 Claims, No Drawings

DIASTEREOMER SALT OF OPTICALLY ACTIVE QUINOLINEMEVALONIC ACID

This is a division of application Ser. No. 08/123,117 filed on Sep. 20, 1993, which is a division of application Ser. No. 07/902,863, filed on Jun. 23, 1992, now U.S. Pat. No. 5,284,953.

The present invention relates to an important intermediate for the preparation of optically active quinolinemevalonic acid derivatives useful for the prevention or treatment of hyperlipemia, arteriosclerosis, etc. and a method for optically resolution thereof.

A quinolinemevalonic acid compound of the formula (V) and a quinolinemevalonolactone compound of the formula (VI):

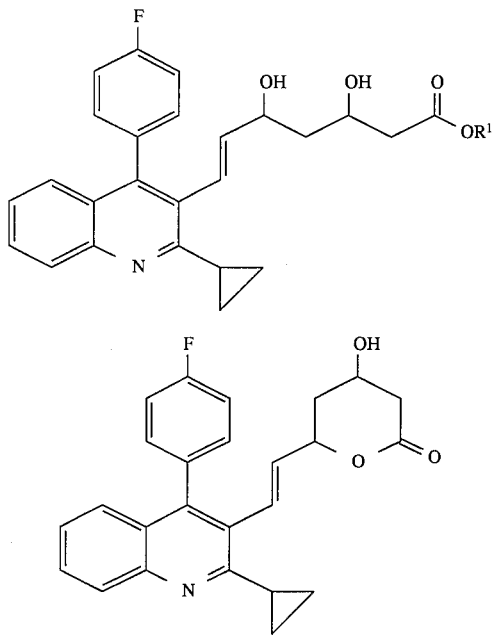

wherein $R^1$ is a hydrogen atom, a $C_{1-4}$ lower alkyl group such as a methyl group, an ethyl group, a n-propyl group, an i-propyl group, a t-butyl group, a n-butyl group, an i-butyl group, a s-butyl group, or Na, K, 1/2 Ca or $HNR^2R^3R^4$ wherein each of $R^2$, $R^3$ and $R^4$ is hydrogen, a $C_{1-3}$ lower alkyl group or a 2-hydroxyethyl group, or when $R^2$ is hydrogen or methyl, $R^3$ and $R^4$ together form $-(CH_2)_4-$, $-(CH_2)_5-$, $-(CH_2)_2-O-(CH_2)_2-$ or $-(CH_2)_2-NH-(CH_2)_2-$, are racemic mixtures or compounds having four optical isomers, as disclosed in Japanese and European Unexamined Patent Publication Nos. 279866/1989 and 304063, and they are strong inhibitors against HMG-CoA reductase which is a rate limiting enzyme for the biosynthesis of cholesterol and thus expected to be useful as drugs for the prevention and treatment of hyperlipemia, arteriosclerosis, etc.

Further, quinolinecarboxylic acid derivatives as HMG-CoA reductase inhibitors are disclosed, for example, in the following literatures: German Patent DE-3905908, U.S. Pat. No. 4,761,419, U.S. Pat. No. 4,923,861 and European Patent Publication EP 356788A.

As disclosed in Japanese and European Unexamined Patent Publication Nos. 279866/1989 and 304063, the compounds of the formulas (V) and (VI) can be prepared as follows:

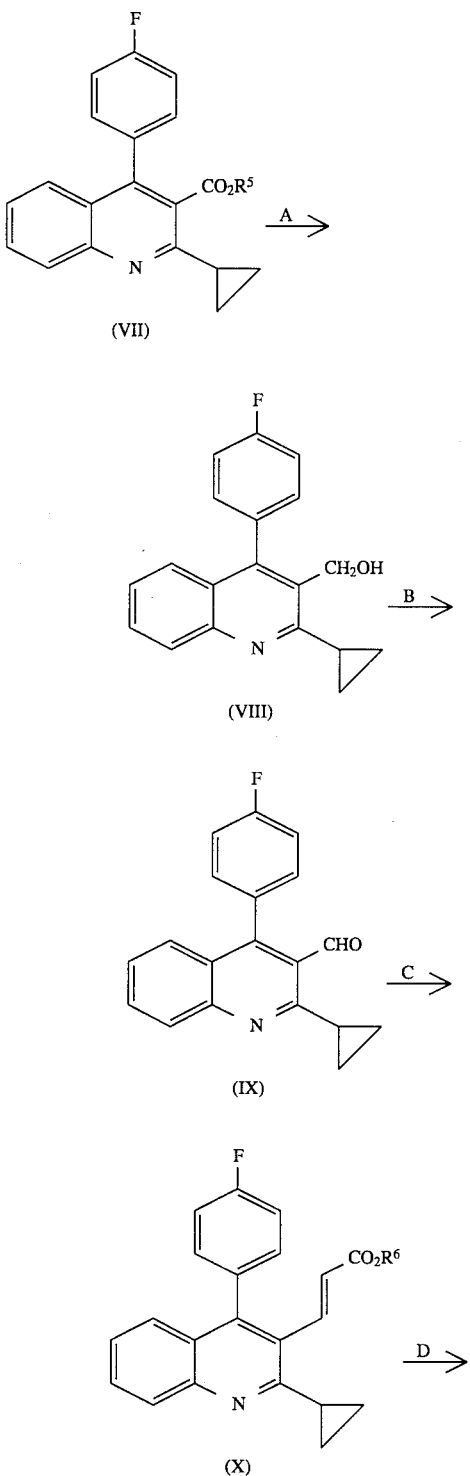

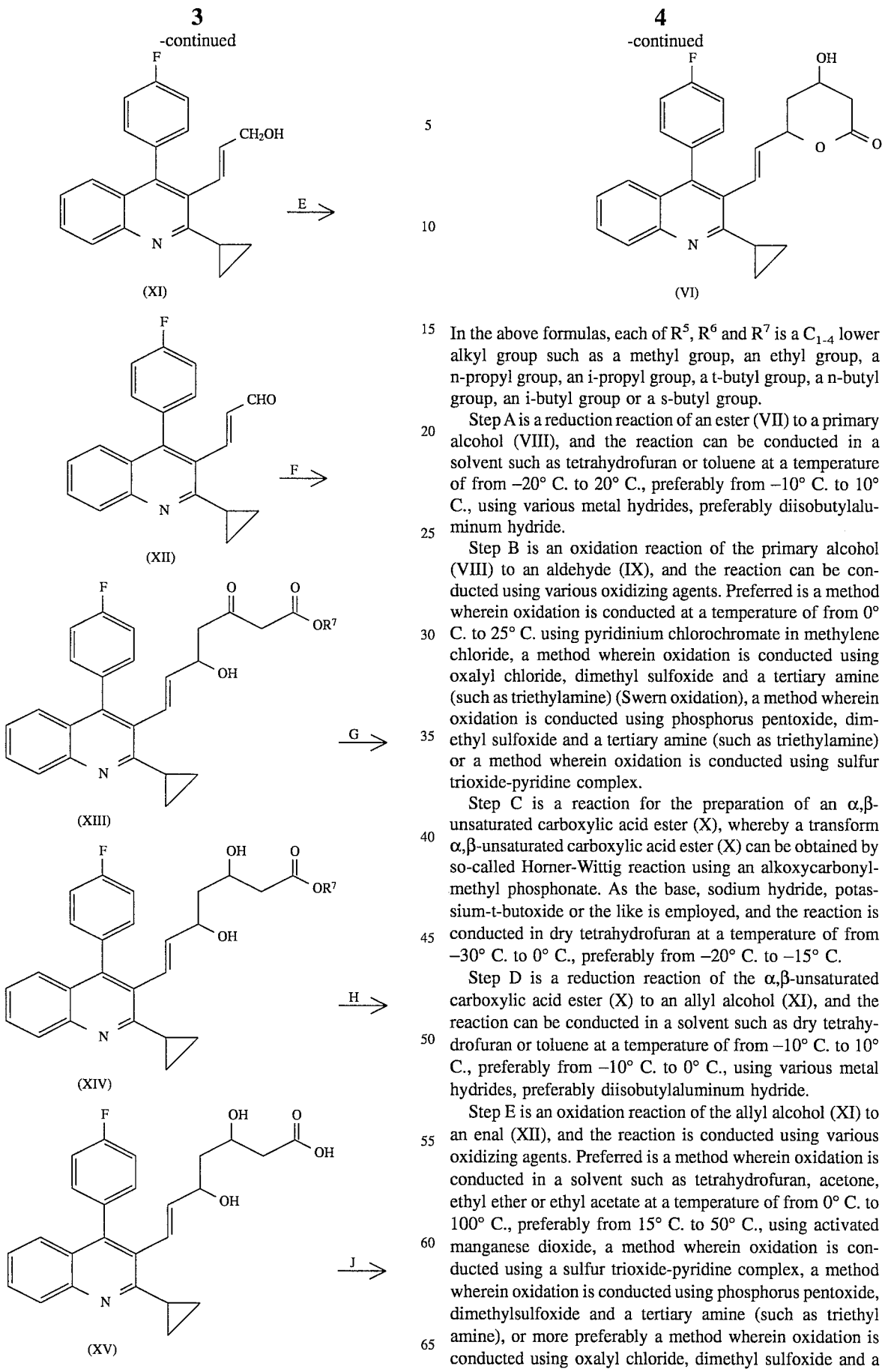

In the above formulas, each of $R^5$, $R^6$ and $R^7$ is a $C_{1-4}$ lower alkyl group such as a methyl group, an ethyl group, a n-propyl group, an i-propyl group, a t-butyl group, a n-butyl group, an i-butyl group or a s-butyl group.

Step A is a reduction reaction of an ester (VII) to a primary alcohol (VIII), and the reaction can be conducted in a solvent such as tetrahydrofuran or toluene at a temperature of from −20° C. to 20° C., preferably from −10° C. to 10° C., using various metal hydrides, preferably diisobutylaluminum hydride.

Step B is an oxidation reaction of the primary alcohol (VIII) to an aldehyde (IX), and the reaction can be conducted using various oxidizing agents. Preferred is a method wherein oxidation is conducted at a temperature of from 0° C. to 25° C. using pyridinium chlorochromate in methylene chloride, a method wherein oxidation is conducted using oxalyl chloride, dimethyl sulfoxide and a tertiary amine (such as triethylamine) (Swern oxidation), a method wherein oxidation is conducted using phosphorus pentoxide, dimethyl sulfoxide and a tertiary amine (such as triethylamine) or a method wherein oxidation is conducted using sulfur trioxide-pyridine complex.

Step C is a reaction for the preparation of an α,β-unsaturated carboxylic acid ester (X), whereby a transform α,β-unsaturated carboxylic acid ester (X) can be obtained by so-called Horner-Wittig reaction using an alkoxycarbonylmethyl phosphonate. As the base, sodium hydride, potassium-t-butoxide or the like is employed, and the reaction is conducted in dry tetrahydrofuran at a temperature of from −30° C. to 0° C., preferably from −20° C. to −15° C.

Step D is a reduction reaction of the α,β-unsaturated carboxylic acid ester (X) to an allyl alcohol (XI), and the reaction can be conducted in a solvent such as dry tetrahydrofuran or toluene at a temperature of from −10° C. to 10° C., preferably from −10° C. to 0° C., using various metal hydrides, preferably diisobutylaluminum hydride.

Step E is an oxidation reaction of the allyl alcohol (XI) to an enal (XII), and the reaction is conducted using various oxidizing agents. Preferred is a method wherein oxidation is conducted in a solvent such as tetrahydrofuran, acetone, ethyl ether or ethyl acetate at a temperature of from 0° C. to 100° C., preferably from 15° C. to 50° C., using activated manganese dioxide, a method wherein oxidation is conducted using a sulfur trioxide-pyridine complex, a method wherein oxidation is conducted using phosphorus pentoxide, dimethylsulfoxide and a tertiary amine (such as triethyl amine), or more preferably a method wherein oxidation is conducted using oxalyl chloride, dimethyl sulfoxide and a tertiary amine (such as triethylamine) (Swern oxidation).

Step F is a condensation reaction of the enal (XII) and a double anion of an acetoacetate, and the reaction is preferably conducted in tetrahydrofuran at a temperature of from −80° C. to 20° C., preferably from −30° C. to 0° C., using sodium hydride as the base and n-butyl lithium.

Step G is a reduction reaction of the carbonyl group of the compound (XIII). There is a method wherein the reduction is conducted in ethanol at a temperature of from −10° C. to 5° C. using a metal hydride, preferably sodium borohydride, a method wherein the reduction is conducted in dry ether or dry tetrahydrofuran at a temperature of from −100° C. to 25° C., preferably from −80° C. to −50° C. using zinc borohydride, and more preferably a method wherein the reduction is conducted in dry tetrahydrofuran-methanol at a temperature of from −80° C. to −60° C. using sodium borohydride and triethylborane or diethylmethoxyborane. (The compound (XIV) corresponds to the compound (V) wherein $R^1$ is a $C_{1-4}$ lower alkyl group.)

Step H is a step for hydroryzing the ester (XIV), which can be conducted in a solvent mixture of methanol or ethanol with water at a temperature of from 10° C. to 25° C. using an equimolar amount of a base, preferably potassium hydroxide or sodium hydroxide. (The compound (XV) corresponds to the compound (V) wherein $R^1$ is a hydrogen atom.)

Step J is a step for forming mevalonolactone by a dehydration reaction of the free hydroxy acid (XV), and the reaction can be conducted using a suitable acid catalyst, preferably trifluoroacetic acid. Otherwise, the reaction can be conducted by removing the resulting water while refluxing in benzene or toluene under heating, or by adding a suitable water-removing agent such as molecular sieves. Further, the reaction can be conducted at a temperature of from 10° C. to 35° C., preferably from 20° C. to 25° C., using a lactone-modifying agent in dry methylene chloride, such as a carbodiimide, preferably a water-soluble carbodiimide such as N-cyclohexyl-N'-[2'-(methylmorpholinium-)ethyl]carbodiimide p-toluenesulfonate.

With respect to drugs, there are many cases in which the pharmacological activities and safety differ among optical isomers. In order to develop an excellent drug, it is desired to separate them by optical resolution.

However, there has been no method for optical resolution known to be industrially useful for the separation of the racemic modification of the quinolinemevalonic acid ((±)I).

The present inventors have discovered that the racemic modification of quinolinemevalonic acid ((±)I) forms a salt with D(+) phenethylamine((+)II) as an optically active amine, whereby the optically active quinolinemevalonic acid ((−)I) can be separated by optical resolution. The present invention has been accomplished on the basis of this discovery.

Thus, the present invention provides a diastereomer salt of optically active quinolinemevalonic acid of the formula ((−)I·(+)II):

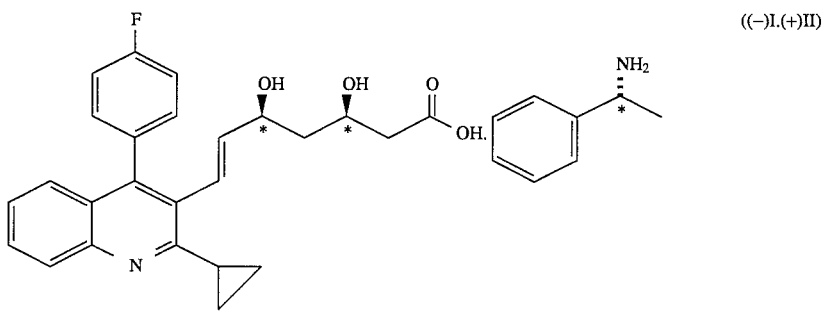

The present invention provides also a method for optical resolution of quinolinemevalonic acid ((±)I), which comprises reacting the quinolinemevalonic acid of the formula ((±)I) with D(+) phenethylamine of the formula ((+)II), and separating the resulting diastereomer salt of optically active quinolinemevalonic acid of the formula ((−)I·(+)II):

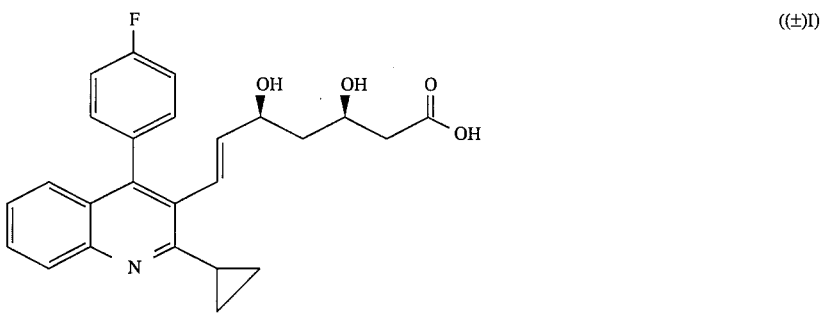

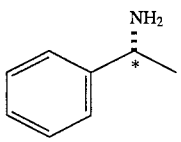 ((+)II)

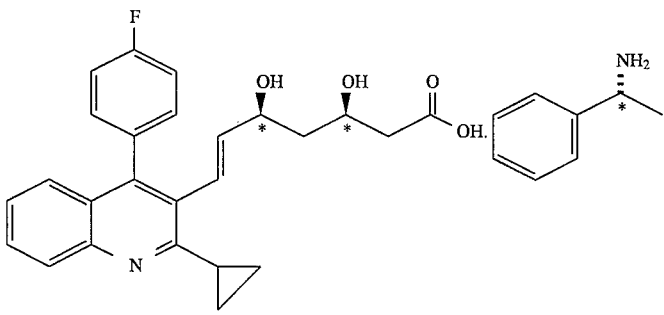 ((−)I·(+)II)

Further, the present invention provides a process for producing optically active quinolinemevalonic acid of the formula ((−)I), which comprises treating the diastereomer, salt of optically active quinolinemevalonic acid of the formula ((−)I·(+)II), with an acid:

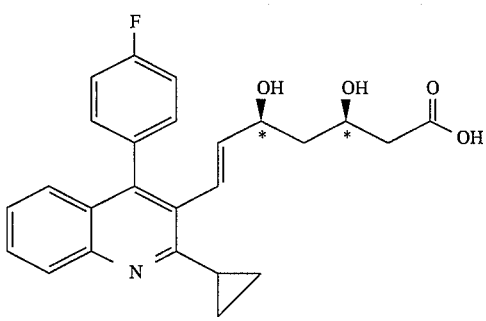 ((−)I)

Still further, the present invention provides a process for producing optically active quinolinemevalonolactone of the formula (III), which comprises dehydrating the optically active quinolinemevalonic acid of the formula ((−)I):

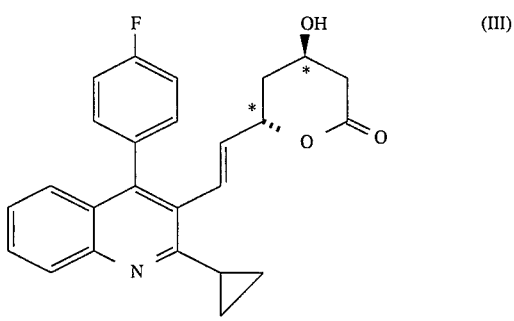 (III)

The present invention further provides a process For producing optically active quinolinemevalonic acid salt of the formula (IV), which comprises reacting the optically active quinolinemevalonic acid of the formula ((−)I), with a base::

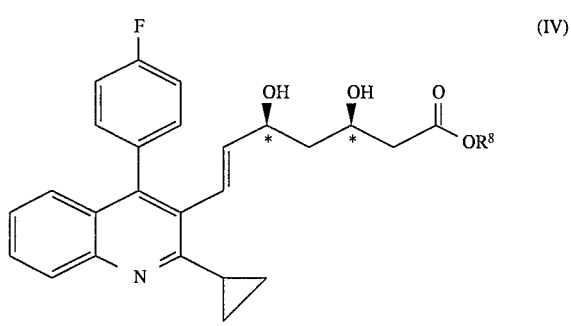 (IV)

wherein $R^8$ is Na, K, 1/2Ca or $HNR^2R^3R^4$ wherein each of $R^2$, $R^3$, $R^4$ is hydrogen, a $C_{1-3}$ lower alkyl group or a 2-hydroxyethyl group, or when $R^2$ is hydrogen or a methyl group, $R^3$ and $R^4$ together form $—(CH_2)_4—$, $—(CH_2)5—$, $—(CH_2)_2—O—(CH_2)_2—$ or $—(CH_2)_2—NH—(CH_2)_2—$.

Furthermore, the present invention provides a process for producing optically active quinolinemevalonic acid salt of the formula (IV), which comprises reacting the diastereomer salt of optically active quinolinemevalonic acid of the formula ((−)I·(+)II), with a base.

Now, the present invention will be described in detail with reference to the preferred embodiments.

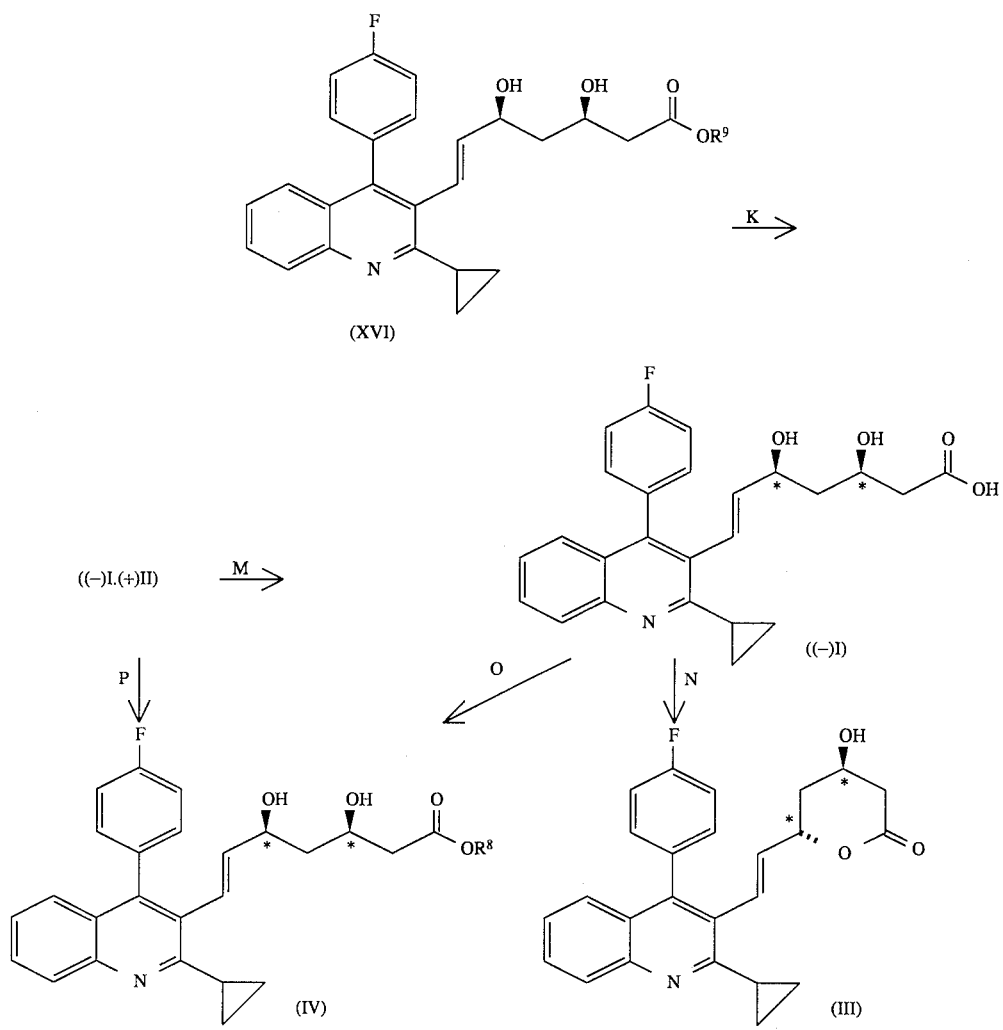

In the above formulas, $R^8$ is Na, K, 1/2 Ca or $HNR^2R^3R^4$, wherein each of $R^2$, $R^3$ and $R^4$ is hydrogen a $C_{1-3}$ lower alkyl group or 8 2-hydroxyethyl group, or when $R^2$ is hydrogen or methyl, $R^3$ and $R^4$ together form —$(CH_2)_4$—, —$(CH_2)_5$—, —$(CH_2)_2$—O—$(CH_2)_2$— or —$(CH_2)_2$—NH—$(CH_2)_2$—, and $R^9$ is a $C_{1-4}$ lower alkyl group, Step K is a step for-hydroryzing a racemic ester (XVI), and the hydrolysis can be conducted in a solvent mixture of methanol or ethanol with water at a temperature of from 0° C. to 25° C. using an equimolar amount of a base, preferably potassium hydroxide or-sodium hydroxide, followed by neutralization using an aqueous acid solution, preferably hydrochloric acid, to obtain a free-quinoline mevalonic acid ((±)I).

Step L is a step for reacting D(+) phenethylamine ((+)II) as an optical resolution agent to the quinolinemevalonic acid ((±)I) for precipitation to obtain the diastereomer salt of optically active quinolinemevalonic acid ((−)I·(+)II) as crystals. Likewise, if L(−)phenethylamine ((−)II) is used as an optical resolution agent, it is possible to obtain a diastereomer salt of optically active quinoline mevalonic acid ((+)I·(−)II). Thus, by selecting the optical resolution agent, a desired optical isomer of the quinolinemevalonic acid ((±)I) can be obtained. As the solvent, a ketone-type solvent such as diethyl ketone or methyl isobutyl ketone, or a solvent such as toluene or xylene may be used alone, or a solvent mixture of such a solvent with an alcohol solvent such as methanol or ethanol, or a solvent such as dimethylformamide or dimethyl sulfoxide, may preferably be used. The reaction temperature is usually from 0° C. to 100° C., and the precipitation is conducted usually at a temperature of from −20° C. to 100° C., preferably from −10° C. to 80° C.

In step M, the optically active quinolinemevalonic acid ((−)I) can readily be obtained by treating the diastereomer salt of optically active quinolinemevalonic acid ((−)I·(+)II) with various aqueous acid solutions. As the acid, formic acid, trifluoroacetic acid or hydrochloric acid is preferred. Particularly preferred is hydrochloric acid.

Step N is a step for forming an optically active quinolinemevalonolactone (III) by a dehydration reaction of the optically active quinolinemevalonic acid ((−)I), and the dehydration reaction can be conducted using an acid catalyst, preferably trifluoroacetic acid. Otherwise, the reaction can be conducted by removing the resulting water while refluxing in benzene or toluene under heating, or by adding a water-removal agent such as molecular sieves. Further, the dehydration can be conducted at a temperature of from 10° C. to 35° C., preferably from 20° C. to 25° C., using a lactone-modification agent in dry methylene chloride, such as a carbodiimide, preferably a water-soluble carbodiimide such as N-cyclohexyl-N'-[2'-(methylmorpholinium)ethyl] carbodiimide p-toluenesulfonate.

Step O is a step of reacting the optically active quinolinemevalonic acid ((−)I) with a base to obtain an optically active quinolinemevalonic acid salt (IV). The base used here may be piperazine, morpholine, diethanolamine, triethanolamine, NaOH, KOH, Ca(OH)$_2$ or CaO.

In step P, the optically active quinolinemevalonic acid salt (IV) can be obtained from the diastereomer salt of optically active quinolinemevalonic acid ((−)I·(+)II) without isolating the optically active quinolinemevalonic acid ((−)I). Namely, by adding an aqueous solution of alkali metal hydroxide (such as sodium hydroxide or potassium hydroxide) to the diastereomer salt of optically active quinolinemevalonic acid ((−)I·(+)II), it is possible to directly obtain an alkali metal salt (such as a quinolinemevalonic acid salt (IV) wherein $R^8$ is Na or K). Further, by adding an aqueous solution of an alkaline earth metal chloride (such as CaCl$_2$) to such an aqueous alkali metal salt solution, it is possible to obtain an alkaline earth metal salt (such as a quinolinemevalonic acid salt (IV) wherein $R^8$ is 1/2Ca).

Now, the present invention will be described in detail with reference to Examples, but it should be understood that the present invention is by no means restricted by such specific Examples.

REFERENCE EXAMPLE 1

(±)-(E)-3,5-dihydroxy-7-[4'-(4''-fluorophenyl)-2'-cyclopropylquinolin-3'-yl]hept-6-ene acid compound ((±)I)

60 g of (±)-(E)-ethyl-3,5-dihydroxy-7-[4'-(4''-fluorophenyl)-2'-cyclopropylquinolin-3'-yl]hept-6-enoate (a compound (XVI) wherein $R^9$ is Et) was suspended in 100 ml of ethanol, and 200 ml of a 1N sodium hydroxide aqueous solution was added thereto. As the reaction proceeded, the suspension became a uniform solution. After completion of the hydrolysis, 200 ml of 1N hydrochloric acid was added thereto. This reaction solution was extracted with 500 ml of dichloromethane to obtain the desired compound ((±)I).

H-NMR(CDCl$_3$), δppm 1.0–1.1 (m, 2H), 1.3–1.4 (m, 3H), 1.5–1.6 (m, 1H), 2.3–2.4(m, 1H), 2.51 (d, 2H, J=6.1), 2.8–3.5 (b, 3H), 4.1–4.2 (m, 1H), 4.4–4.5(m, 1H), 5.59 (dd, 1H, J=6.1, J=16.1), 6.63 (d, 1H, J=6.1), 7.1–7.4 (m, 6H), 7.5–7.7 (m, 1H), 7.9–8.0 (m, 1H).

REFERENCE EXAMPLE 2

Resolution of a diastereomer salt using a chiral organic amine

To the dichloromethane solution of the compound ((±)I) obtained in Reference Example 1, 1 equivalent of a chiral organic amine as identified in Table 1 was added, and then the solvent was distilled off to obtain a residue containing the corresponding diastereomer salt. Except for the case where the residue was oil, the residue was dissolved under heating in ten times by weight of methyl isobutyl ketone-dimethylformamide (20:1, v/v), followed by cooling to a temperature of from 10 to 25° C. for crystallization. For the optical yield, the obtained diastereomer salt was treated with an acid and then converted to lactone, and the optical yield was measured by a high performance liquid chromatography using an optical resolution column (chiraSpher, tradename, manufactured by E. Merck Company).

| Resolution agent (chiral organic amine) | Chemical yield (%) | Optical yield (% ee) |
| --- | --- | --- |
| D(+)phenethylamine | 44 | 73 |
| R(+)α-(p-tolyl)ethylamine | 30[1] | 60 |
| R(−)2-amino-1-butanol | 80 | 0 |
| D(−)α-phenylglycinol | —[2] | — |
| (−)N-benzyl-α-phenylethylamine | —[2] | — |
| (−)p-bromo-α-phenylehtylamine | —[2] | — |

[1] A gel substance precipitated.
[2] The diastereomer salt was an oily substance.

EXAMPLE 1

(E)-3(R)-5(S)-dihydroxy-7-[4'-(4''-fluorophenyl)-2'-cyclopropylquinolin-3'-yl]hept-6-ene acid·D(+) phenethylamine salt compound ((−)I·(+)II)

To the dichloromethane solution of the compound ((±)I) obtained in Reference Example 1, 16.2 g of D(+) phenethylamine ((+)II) was added, and the mixture was stirred. Then, dichloromethane was distilled off to obtain a residue. The residue was repeatedly crystallized from methyl isobutyl ketone and methyl isobutyl ketone-ethanol (10:1, v/v) to obtain 19.8 g of the desired compound ((−)I·(+)II) as white crystals. (Melting point: 144°–147° C., optical purity: 97% ee.)

EXAMPLE 2

(E)-6(S)-[4'-(4''-flurophenyl)-2'-cyclopropylquinolin-3'-ylethenyl]-4(R)-hydroxy-3,4,5,6-tetrahydro-2H-pyran-2-one compound (III)

To 14.08 g of (E)-3(R)-5(S)-dihydroxy-7-[4'-(4''-fluorophenyl)-2'-cyclopropylquinolin-3'-yl]hept-6-ene acid-D(+) phenethylamine salt compound ((−)I·(+)II) obtained in Example 1, 25.9 ml of 1N hydrochrolic acid and 235 ml of water were added, and the compound was dissolved. To this solution, 250 ml of ethyl acetate was added to extract the compound ((−)I). The ethyl acetate solution was washed with a saturated sodium chloride aqueous solution, and the solvent was distilled off under reduced pressure. To the residue, 250 ml of dry toluene was added and refluxed under heating for 3 hours by means of a Dean Stark apparatus. The solvent was distilled off under reduced pressure, and the residual solid thereby obtained was recrystallized from toluene-heptane to obtain 6.4 g of the desired compound (III). (Melting point: 136°–139° C.).

EXAMPLE 3

(E)-3-(R)-5(S)-dihydroxy-7-[4'-(4''-fluorophenyl)-2'-cyclopropylquinolin-3'-yl]hept-6-ene acid·½ calcium salt To 12.0 g of (E)-3(R)-5(S)-dihydroxy-7-[4'-(4''-fluorophenyl)-2'-cyclopropylquinolin-3'-yl]hept-6-ene acid·D(+) phenethylamine salt compound ((−)I·(+)II)

obtained in Example 1, 24.3 ml of a 1N sodium hydroxide aqueous solution and 200 ml of water were added and stirred to dissolve the compound. To this solution, an aqueous calcium chloride solution obtained by dissolving 1.47 g of dry calcium chloride to 200 ml of water, was dropwise added. This reaction solution was stirred overnight, and the resulting white precipitate was collected by filtration to obtain 9.0 g of white crystals (melting point: 190°–192° C. (decomposed)).

We claim:

1. A process for producing optically active quinolinemevalonolactone of the formula (III):

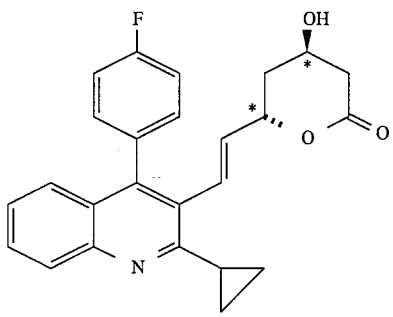

which comprises dehydrating an optically active quinolinemevalonic acid of the formula ((–)I):

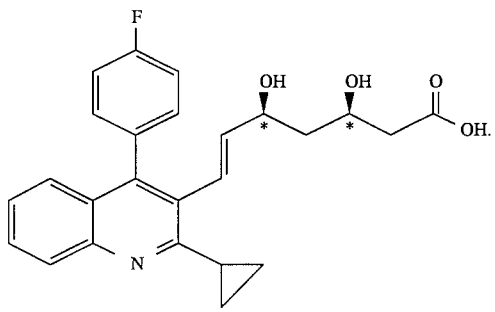

2. A process for producing an optically active quinolinemevalonic acid salt of the formula (IV):

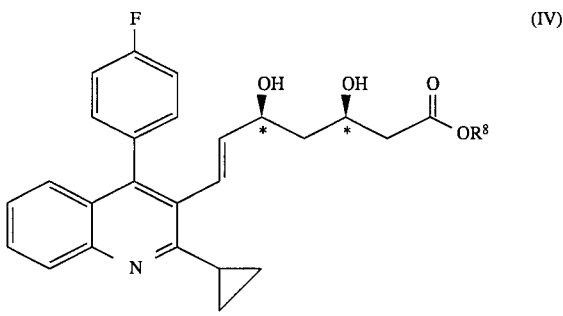

which comprises reacting an optically active quinolinemevalonic acid of the formula ((–)I):

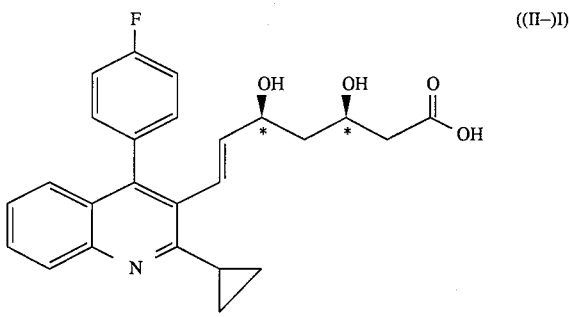

with a base, wherein $R^8$ is Na, Ka, ½ Ca or $HNR^2R^3R^4$, wherein each of $R^2$, $R^3$ and $R^4$ is hydrogen, $C_1$–$C_3$ lower alkyl or 2-hydroxyethyl; or when $R^2$ is hydrogen or methyl, $R^3$ and $R^4$ together form —$(CH_2)_4$—, —$(CH_2)_5$—, —$(CH_2)_2$—O—$(CH_2)_2$— or —$(CH_2)_2$—NH—$(CH_2)_2$—.

3. The process for producing the optically active quinolinemevalonic acid salt of the formula (IV) as defined in claim 2, which comprises reacting the diastereomer salt of optically active quinolinemevalonic acid of the formula ((–)I·(+)II) as defined below, with a base:

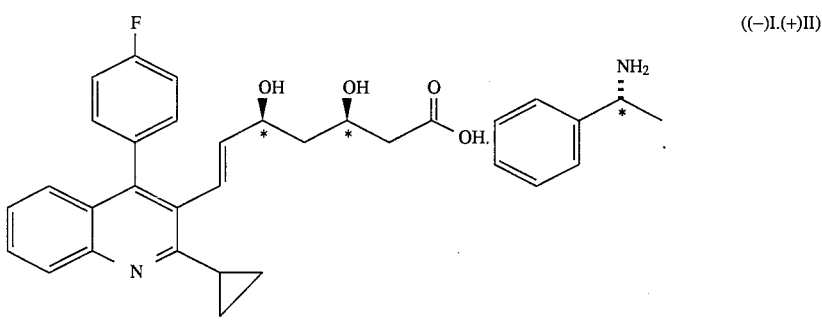

4. The process of claim 1, wherein said dehydration is effected using an acid catalyst.

5. The process of claim 1, wherein said dehydration is effecting using a carbodiimide.

6. The process of claim 1, wherein said dehydration is effected at a temperature of form 10° C. to 35° C.

7. The process of claim 2, wherein said base is selected from the group consisting of piperazine, morpholine diethanolamine, triethanolamine, NaOH, KOH, $Ca(OH_2)$ and CaO.

8. The process of claim 3, wherein said base is an alkali metal hydroxide.

* * * * *